US00PP26651P3

(12) United States Plant Patent
Fourie et al.

(10) Patent No.: US PP26,651 P3
(45) Date of Patent: Apr. 26, 2016

(54) GRAPE PLANT NAMED 'STARGRAPE 1'

(50) Latin Name: ***Vitis vinifera* L.**
Varietal Denomination: Stargrape 1

(71) Applicant: Stargrow Cultivar Development (Pty) Ltd, Stellenbosch (ZA)

(72) Inventors: Jeanne Fourie, Stellenbosch (ZA); Phil Ellis, Stellenbosch (ZA)

(73) Assignee: Stargrow Cultivar Development (PTY) Ltd, Stellenbosch (ZA)

( * ) Notice: Subject to any disclaimer, the term of this patent is extended or adjusted under 35 U.S.C. 154(b) by 55 days.

(21) Appl. No.: 13/999,669

(22) Filed: Mar. 13, 2014

(65) Prior Publication Data

US 2014/0283241 P1 Sep. 18, 2014

Related U.S. Application Data

(60) Provisional application No. 61/852,408, filed on Mar. 15, 2013.

(51) Int. Cl.
*A01H 5/00* (2006.01)
*A01H 5/08* (2006.01)

(52) U.S. Cl.
USPC ..... Plt./205
CPC ..... *A01H 5/0812* (2013.01)

(58) Field of Classification Search
USPC ..... Plt./205
See application file for complete search history.

*Primary Examiner* — Annette Para
(74) *Attorney, Agent, or Firm* — Michelle Bos Legal LLC

(57) ABSTRACT

A new table grape plant named 'Stargrape 1', notable for its improved natural color, excellent berry size, and reduced susceptibility to cracking.

4 Drawing Sheets

Latin name: *Vitis vinifera* L.
Variety denomination: 'Stargrape 1'.

BACKGROUND OF THE VARIETY

'Stargrape 1' is a new and distinct variety of table grape plant (*Vitis vinifera* L.) of unknown parentage. 'Stargrape 1', which originated as an open cross, was first selected at Clanwilliam, South Africa in 2003, and was subsequently asexually reproduced by grafting in 2005 and fruited through successive generations at the same location. 'Stargrape 1' has been observed to remain true to type over successive asexually propagated generations.

BRIEF DESCRIPTION OF THE VARIETY

'Stargrape 1' was first selected for its excellent color and berry size. It is distinguished from 'Flame Seedless' (not patented) by its improved natural color, berry size, and reduced susceptibility to cracking.

The following table shows a comparison of 'Stargrape 1' to similar varieties 'Stargrape 2' and 'Flame Seedless':

| | 'Stargrape 1' | 'Stargrape 2' | 'Flame Seedless' |
|---|---|---|---|
| Skin color | Grey-purple 187A | Grey-purple 183A and 187A | Rose to red |
| % Fully colored berries/bunch | 100% | 90% to 100% | 50% to 70% |
| Berry length | 23 to 27 mm | 21 to 25 mm | 18 to 19 mm |
| Berry width | 19 to 22 mm | 19 to 20 mrn | 16 to 18 mm |
| Berry shape | Broad ellipsoid to narrow ellipsoid | Narrow ellipsoid | Globose |
| Resistance to cracking | More resistant than 'Flame Seedless' | Susceptible | Susceptible |

BRIEF DESCRIPTION OF THE PHOTOGRAPHS

Figure 1:
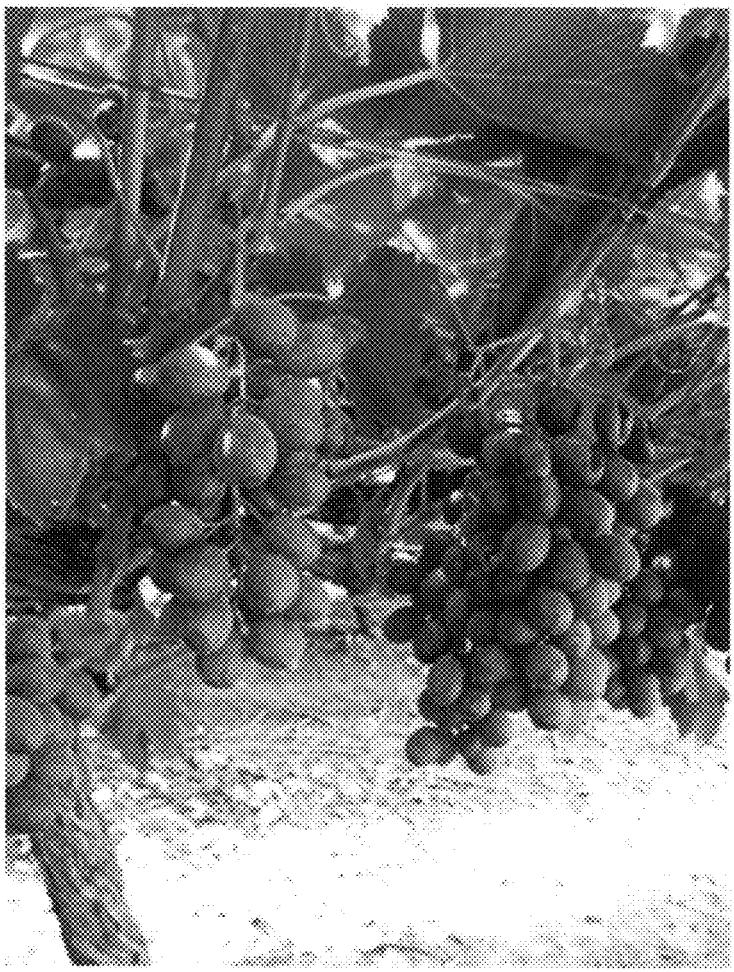
Figure 2:
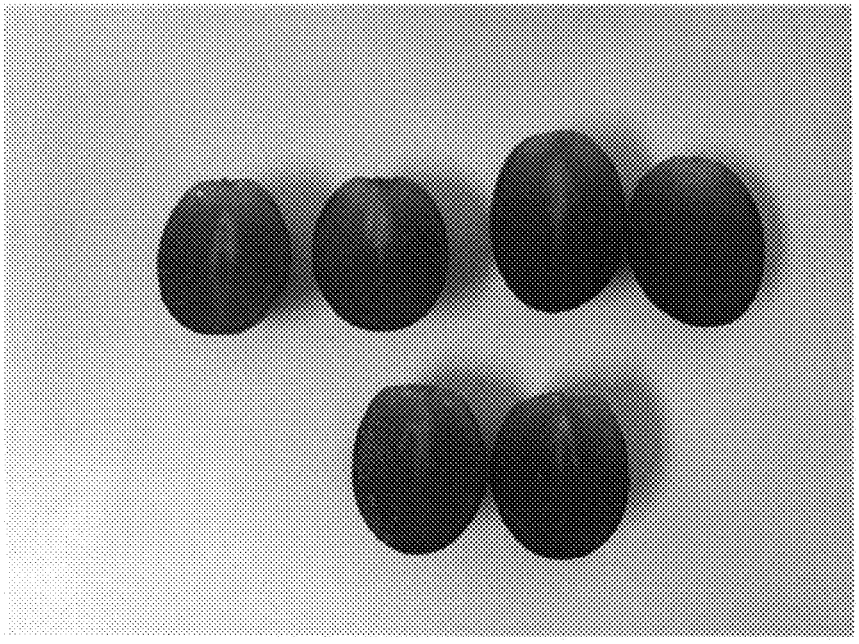
Figure 3:
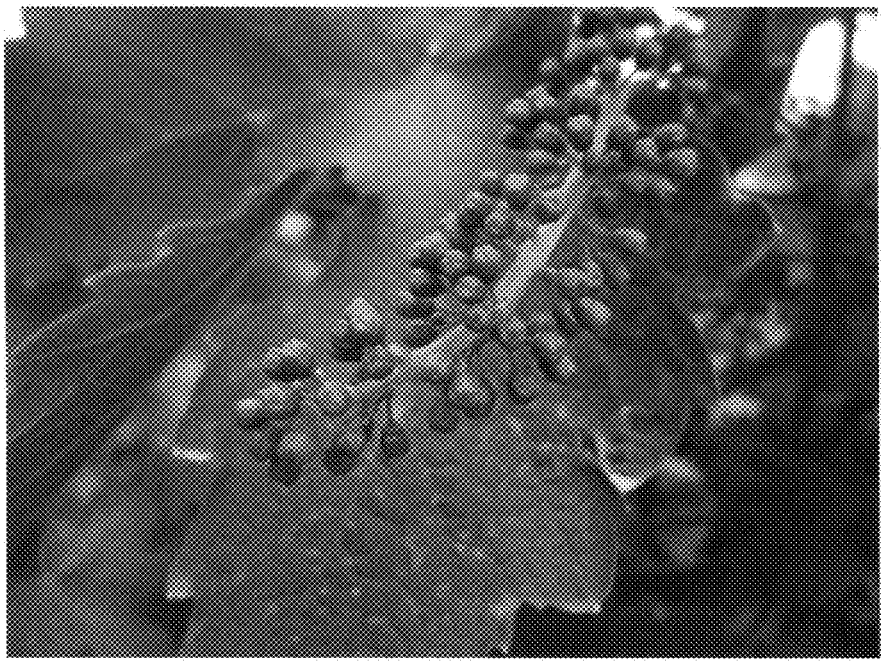
Figure 4:
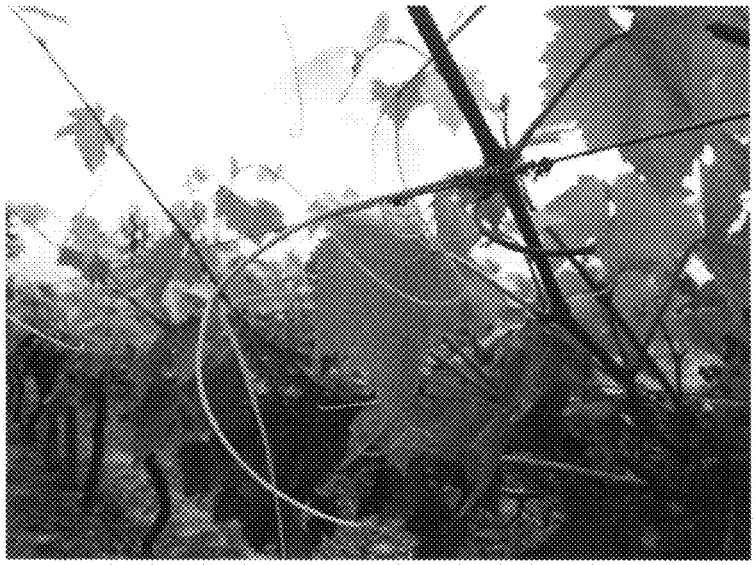
Figure 5:
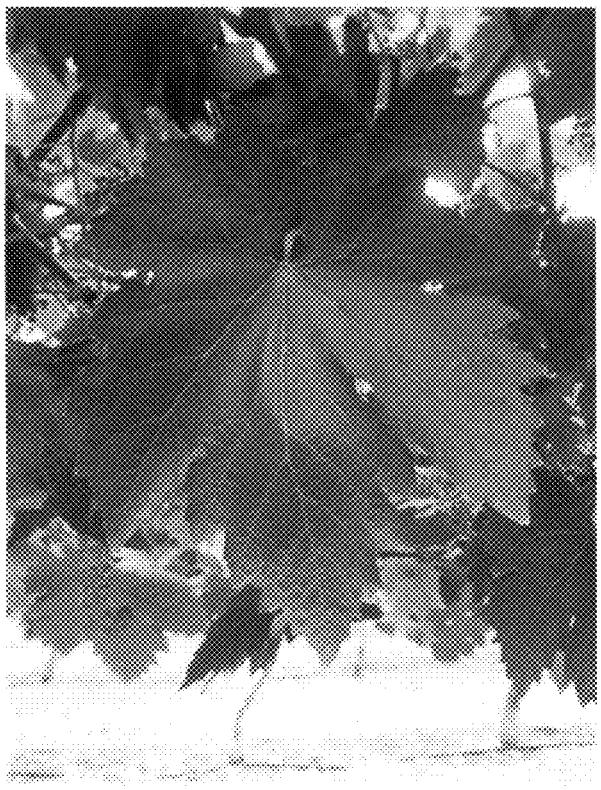
Figure 6:
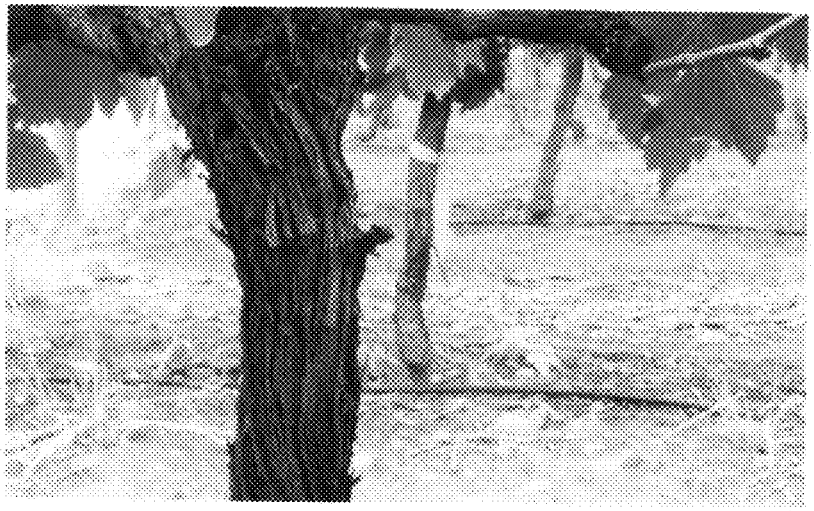
Figure 7:
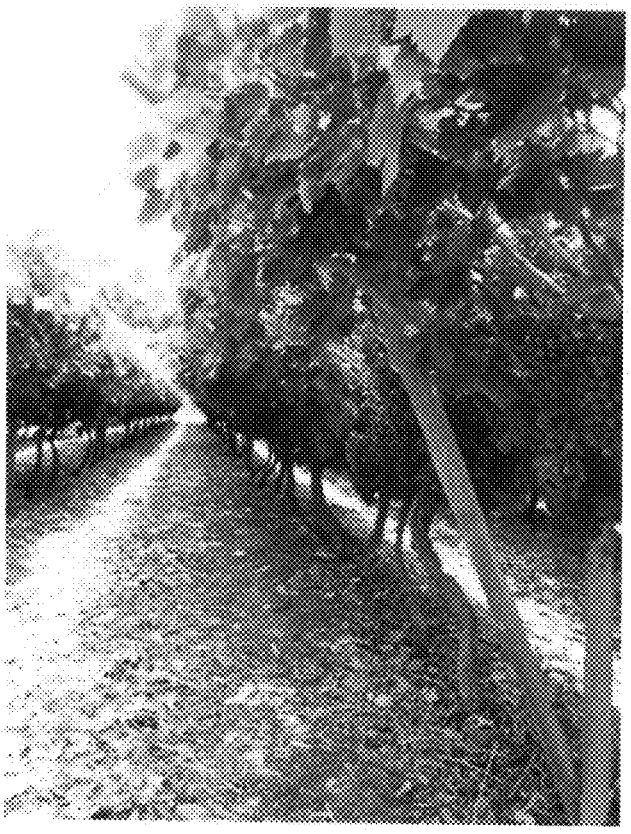

FIG. 1 shows the fruit of 'Stargrape 1' on the vine;
FIG. 2 shows sectioned fruit of 'Stargrape 1';
FIG. 3 shows buds of 'Stargrape 1';
FIG. 4 shows leaves and tendrils of 'Stargrape 1';
FIG. 5 shows a leaf of 'Stargrape 1';
FIG. 6 shows the trunk of 'Stargrape 1'; and
FIG. 7 shows producing vines of 'Stargrape 1'.

DETAILED BOTANICAL DESCRIPTION OF THE VARIETY

The following-detailed botanical description is based on observations made during the 2011/2012 and 2013/2014 growing seasons at Clanwilliam and Wellington, South Africa (USDA Hardiness Zone 10) of 3- to 5-year old vines planted in a commercial vineyard in 2008 on 'Ramsey' rootstock (not known to be patented). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average. Color descriptions are made with reference to The Royal Horticultural Society Colour Chart ($5^{th}$ Edition).

Vine:

*Size.*—Large — height 115 cm with 4 cordons; similar to 'Flame'.
*Vigor.*—Strong.
*Timing of bud burst.*—Early to mid-September.
*Productivity.*—Productive.
*Trunk diameter* (50 *cm above ground*).—7 cm.
*Bark texture.*—Rough.
*Bark color.*—Brown N200A.

Canes:
*Size (diameter).*—68 mm to 89 mm.
*Quantity.*—5 to 6 canes per cordon.
*Bark color.*—Greyed orange 164B.
*Bark texture.*—Smooth.
*Form.*—Semi-erect.
*Node size.*—Thick, 13 mm to 15 mm.
*Internode length.*—Long, 130 mm to 140 mm.
*Quantity of tendrils per node.*—1.
*Tendril thickness.*—Medium to thick, 3 mm.
*Tendril length.*—Medium to long, 200 to 250 mm.
*Tendril texture.*—Smooth.

Flowers:
*Fertility.*—Self fertile.
*Date of bloom.*—Medium, late October to early November.
*Filament length.*—2.1 mm to 2.5 mm.
*Filament color.*—Yellow-green N144B.
*Anther length.*—1.0 mm to 1.2 mm.
*Anther color.*—Yellow-green N144B.
*Pistil length.*—0.5 to 0.7 mm.
*Pistil color.*—Green 135B.
*Flower stem length.*—3.9 mm to 4.4 mm.
*Flower stem color.*—Green 135B.
*Flower type.*—Fully developed stamens and gynoecium.
*Stamen color.*—Yellow-green 151B.
*Stamen length.*—2.8 mm to 4.1 mm.
*Stamen quantity.*—5 to 6.

Leaves:
*Relative size.*—Medium.
*Length.*—Medium, 174 mm.
*Width.*—Broad, 210 mm.
*Thickness.*—0.2 mm.
*Shape.*—Wedge-shaped.
*Color — upper surface.*—Green 137A.
*Color — lower surface.*—Green 138A.
*Texture.*—Somewhat smooth.
*Number of lobes.*—Five.
*Terminal lobe form.*—Similar to 'Flame'.
*Petiole color.*—Yellow-green N144C.
*Petiole sinus depth.*—75 mm.
*Petiole sinus shape.*—U-shaped; similar to 'Flame'.
*Petiole length.*—Medium to long, 145 mm.
*Lateral sinus depth.*—Shallow to medium, 30 mm.
*Lateral sinus — relative arrangement of lobes.*—Open to slightly overlapped.
*Shape of teeth.*—Mixed: some with both sides straight, and some with both sides convex.

Tendrils:
*Quantity.*—Three on a 70 cm shoot.
*Thickness.*—3 mm.
*Length.*—200 mm to 250 mm.
*Form.*—Mild spiral.
*Texture.*—Smooth.
*Color.*—Yellow-green N144A.

Shoot:
*Attitude (before tying).*—Semi-erect.
*Color.*—Green 143A.
*Hairs on internodes.*—Absent or very sparse.

Fruit:
*Maturity date.*—Medium, early January.
*Shape.*—Broad elliptic to narrow elliptic.
*Length.*—Medium, 23 mm to 27 mm (10 ppm Gibb).
*Width.*—Medium, 19 mm to 22 mm (10 ppm Gibb).
*Relative size.*—Medium.
*Brix.*—16%.
*Skin thickness.*—Medium.
*Skin color.*—Grey-purple 187A.
*Flesh color.*—Yellow-green 145D.
*Flesh texture.*—Slightly firm.
*Juice production.*—Juicy.
*Anthocyanin coloration.*—Absent or very weak.
*Flavor.*—Neutral.
*Seeds.*—Present, rudimentary.
*Seed size.*—2.9 to 3.3 mm.
*Seed shape.*—Not completely formed.
*Seed color.*—Rudimentary, Yellow-green N144C.

Cluster:
*Overall shape.*—Long, well-filled.
*Relative size.*—Medium.
*Length.*—Medium, 200 mm to 250 mm.
*Width.*—Medium, 130 mm to 170 mm.
*Peduncle length.*—Short, 40 mm.
*Peduncle thickness.*—3.7 mm to 4.1 mm.
*Pedicel length.*—Medium, 10.1 mm to 13.2 mm.
*Pedicel thickness.*—Medium, 2.5 mm.

Storage quality: Good.
Shipping quality: Good.
Disease/insect resistance/susceptibility: Similar to 'Flame Seedless'.

We claim:
1. A new and distinct grape plant substantially as described and illustrated herein.

* * * * *